United States Patent
Cotton et al.

(10) Patent No.: US 9,254,354 B2
(45) Date of Patent: Feb. 9, 2016

(54) DEVICE AND METHOD FOR PROCESSING FLUID

(75) Inventors: Stephen Cotton, Nottingham (GB); Terence Gourlay, Glasgow (GB)

(73) Assignee: Brightwake Limited, Nottingham, Nottinghamshire (GB)

( * ) Notice: Subject to any disclaimer, the term of this patent is extended or adjusted under 35 U.S.C. 154(b) by 705 days.

(21) Appl. No.: 13/384,135

(22) PCT Filed: Nov. 17, 2010

(86) PCT No.: PCT/GB2010/051916
§ 371 (c)(1), (2), (4) Date: Mar. 30, 2012

(87) PCT Pub. No.: WO2011/061533
PCT Pub. Date: May 26, 2011

(65) Prior Publication Data
US 2012/0175319 A1    Jul. 12, 2012

(30) Foreign Application Priority Data

Nov. 17, 2009 (GB) .................................. 0920069.2
Nov. 17, 2009 (GB) .................................. 0920070.0
Nov. 17, 2009 (GB) .................................. 0920072.6

(51) Int. Cl.
*A61M 1/02* (2006.01)
*B01D 29/13* (2006.01)
(Continued)

(52) U.S. Cl.
CPC ............. *A61M 1/0281* (2013.01); *A61J 1/10* (2013.01); *A61J 1/1462* (2013.01); *A61M 1/0209* (2013.01)

(58) Field of Classification Search
CPC ..... A61M 1/0209; A61M 1/0281; A61J 1/10; A61J 1/1462
USPC .......... 210/483, 484, 488; 604/403, 406, 408, 604/409, 410, 416
See application file for complete search history.

(56) References Cited

U.S. PATENT DOCUMENTS

| 3,485,751 | A | 12/1969 | Herrmann et al. |
| 3,742,946 | A | 7/1973 | Grossman |
| 4,183,811 | A | 1/1980 | Walch et al. |

(Continued)

FOREIGN PATENT DOCUMENTS

| EP | 0070738 A1 | 7/1982 |
| EP | 0953361 A1 | 4/1999 |

(Continued)

OTHER PUBLICATIONS

Juliano C. et al. "Preparation and Characterisation of Polymeric Films Containing Propolis," J. of Drug Delivery Science and Tech. 17(3):177-181 (2007).

(Continued)

*Primary Examiner* — John Kim
(74) *Attorney, Agent, or Firm* — LeClairRyan, a Professional Corporation

(57) ABSTRACT

Devices for concentrating fluids that comprise discrete or particulate material dispersed in a liquid medium, such as whole blood, by removal of a proportion of the liquid medium, and a method of producing blood cell concentrates from whole blood using reduced pressure. The devices comprise an outer bag formed of an impermeable material and an inner bag formed of a permeable material, the inner bag containing an absorbent material or being adapted for connection to a source of reduced pressure.

9 Claims, 3 Drawing Sheets

(51) Int. Cl.
*A61J 1/10* (2006.01)
*A61J 1/14* (2006.01)

(56) References Cited

U.S. PATENT DOCUMENTS

| | | |
|---|---|---|
| 4,206,050 A | 6/1980 | Walch et al. |
| 4,631,050 A | 12/1986 | Reed et al. |
| 4,898,572 A | 2/1990 | Surugue nee Lasnier et al. |
| 4,966,758 A | 10/1990 | Belt |
| 5,045,207 A | 9/1991 | Fecondini et al. |
| 5,211,850 A | 5/1993 | Shettigar et al. |
| 5,858,238 A | 1/1999 | McRea et al. |
| 5,876,611 A | 3/1999 | Shettigar |
| 6,153,104 A | 11/2000 | Robertson |
| 6,221,264 B1 | 4/2001 | Ishida et al. |
| 8,187,465 B2 | 5/2012 | Nierich |
| 2004/0007540 A1 | 1/2004 | Verpoort et al. |
| 2004/0081588 A1 | 4/2004 | Hammerstedt et al. |
| 2004/0251195 A1 | 12/2004 | Oka et al. |
| 2004/0258765 A1 | 12/2004 | Gee |
| 2005/0133439 A1 | 6/2005 | Blickhan |
| 2005/0133447 A1 | 6/2005 | Tsai et al. |
| 2006/0054557 A1 | 3/2006 | Hori et al. |
| 2006/0175242 A1 | 8/2006 | Dorian et al. |
| 2009/0300933 A1* | 12/2009 | Howe et al. .................. 34/60 |

FOREIGN PATENT DOCUMENTS

| | | |
|---|---|---|
| EP | 1579838 A1 | 9/2005 |
| FR | 2821762 A1 | 9/2002 |
| JP | 06321722 A | 5/1993 |
| WO | 93/01858 A1 | 2/1993 |
| WO | 9819722 A1 | 5/1998 |
| WO | 0224256 A1 | 3/2002 |
| WO | 03078023 A1 | 9/2003 |
| WO | 2006/021728 A1 | 3/2006 |
| WO | 2006/062808 A2 | 6/2006 |
| WO | 2009/141589 A1 | 11/2009 |

OTHER PUBLICATIONS

Great Britain Search Report for 0911402.6, dated Nov. 2, 2009.
International Search Report for PCT/GB2010/051916, dated Mar. 3, 2011.

* cited by examiner

DEVICE AND METHOD FOR PROCESSING FLUID

This application is a national stage application under 35 U.S.C. §371 from PCT Application No. PCT/GB2010/051916, filed Nov. 17, 2010, which claims the priority benefit of Great Britain Application Nos. 0920072.6, filed Nov. 17, 2009; 0920070.0, filed Nov. 17, 2009; and 0920069.2, filed Nov. 17, 2009

The present invention relates to devices and methods of processing fluids. More particularly, the present invention relates to devices for concentrating fluids comprising discrete or particulate material dispersed in a liquid medium (eg blood) by removal of a proportion of the liquid medium (eg blood plasma), as well as methods of producing blood cell concentrates.

In numerous industrial and commercial situations it is desirable to concentrate fluids comprising discrete or particulate material dispersed in a liquid medium by removal of a proportion of the liquid medium. In particular, whole blood is often processed into a blood cell concentrate by removal of a proportion of the plasma. This is generally carried out by centrifugation of whole blood to separate blood cells from the plasma, allowing removal of the plasma without loss of the blood cells. However, centrifuges capable of effectively separating blood in this way are generally cumbersome and expensive to purchase and operate. Centrifugation of blood is also undesirable as it may lead to lysis of blood cells and/or leukocyte activation.

There has now been devised a fluid concentration device that overcomes or substantially mitigates the above mentioned and/or other problems associated with the prior art.

According to the first aspect of this invention, there is provided a fluid concentration device comprising an outer bag formed of an impermeable material, an inner bag formed of a permeable material and containing an absorbent material, wherein the inner bag is fastened to, and suspended within, the outer bag.

The device of this invention is advantageous primarily in that it provides a self-contained, simple and inexpensive means of effectively concentrating fluids comprising discrete or particulate material dispersed in a liquid medium by removal of a proportion of the liquid medium. The material of the inner bag may allow the liquid medium, but not the discrete or particulate material, to pass into the inner bag and be held there by the absorbent material, thereby increasing the concentration of the discrete or particulate material outside the inner bag.

The device of this invention is particularly effective as the inner bag is fastened to and suspended within the outer bag, which prevents the inner bag slumping or collapsing and so maintains a large effective surface area of the inner bag on the interior of the device.

The device of this invention may be used for any purpose where there is a need to concentrate a fluid comprising particulate or discrete material dispersed in a liquid medium. However, the device of this invention is of particular utility in the field of medicine to produce blood cell concentrates from whole blood by the removal of a proportion of the plasma component.

The materials used to form the inner and outer bags are preferably flexible, to enable the bags to expand to accommodate fluid.

Both the inner and outer bags are preferably formed from two sheets of material fastened together around their edges. This fastening process is preferably performed by heat welding to avoid introducing contaminants, such as adhesives, into the bag. The materials used to form the inner and outer bags are therefore preferably heat weldable.

The outer bag may be formed of any suitable material, but preferred materials are tough and impermeable to reduce the risk of fluid contained within the device from leaking out or becoming contaminated. The outer bag is preferably formed of sheets of synthetic plastic, such as polyethylene, polyamide, polypropylene, polyurethane, polyester or polycarbonate. A particularly preferred material for the outer bag is polyvinylchloride (PVC) in sheet form.

The thickness of the material of the outer bag can be varied depending on the desired properties. The thickness of the material of the outer bag is typically between 0.2 mm and 3 mm, more commonly between 0.5 mm and 2 mm, and preferably about 1 mm.

The fluid may be introduced into the device via a port in the outer bag. Fluid may also be discharged from the device through the same port, or through a second port. The presence of a second port enables fluid to be passed through the device continuously.

The inner bag may be formed of any suitable material able to form a porous layer which allows liquid medium to pass through without the inner bag losing its integrity. The inner bag is preferably formed of sheets of synthetic plastic, such as polyethylene, polyamide, polypropylene, polyurethane, polyester or polyvinylchloride (PVC). One particularly preferred material for the inner bag is porous polycarbonate membrane.

The thickness of the material of the inner bag is typically between 0.1 mm and 2 mm, more commonly between 0.2 mm and 1 mm, and preferably about 0.5 mm.

The porous material of the inner bag may allow liquid medium to pass through, but substantially prevent the passage of the discrete or particulate material dispersed in the liquid medium. Where the discrete or particulate material is present in a range of sizes, the porous material may allow the particles at the lower end of the size range to pass through. The inner bag is preferably completely sealed so the liquid medium is only able to enter the inner bag by passing through its porous walls.

The size of the pores in the porous material may be varied to suit the specific application of the device, but the diameter of the pores typically ranges from 0.01 μm to 1 mm or more, more particularly 0.01 μm to 5 μm, and most particularly 0.1 μm to 2 μm. Where the device is used to concentrate blood, the pores of the inner bag should have a diameter of no greater than about 1 μm in order to retain substantially all the particulate matter of the blood in the cavity between the outer bag and the inner bag. It is preferred for the pores to be of a generally uniform size, but a range of pore sizes to be present.

The fluid concentrating activity of the device requires the fluid entering the device to contact the inner bag, so the inner bag preferably presents the largest possible effective surface area on the interior of the device. This is achieved by suspending the inner bag within the outer bag by fastening the inner bag to the outer bag. This prevents the inner bag slumping or collapsing, which would reduce the effective surface area of the inner bag on the interior of the device.

In one particularly preferred embodiment, the inner bag is suspended within the outer bag at one or more fastening points that comprise a tab projecting from the edge of the inner bag sandwiched between the two layers of the outer bag in a region where the layers of the outer bag are welded together. Where the materials used for the inner and outer bags do not readily weld to one another, the tab may be provided with one or more apertures to allow the two layers of the outer bag to weld together through the tab in order to anchor the tab in position. This is particularly preferable because the most preferred materials for forming the outer and inner bags, PVC and polycarbonate, do not weld strongly to one another.

The most suitable absorbent materials for use with the present invention are of the type commonly referred to as a "superabsorbers" or "superabsorbent materials". Such materials are typically polymers that are capable of absorbing and retaining extremely large quantities of fluid relative to their own mass. Typically, such materials absorb aqueous solutions through hydrogen bonding with water molecules, and may absorb up to 200, 400, or 500 times or more their weight of water.

Amongst the most commonly used superabsorbent polymers are polyacrylates, ie salts of polyacrylic acid. For instance, the sodium salt of polyacrylic acid (cross-linked sodium polyacrylate) may be produced by the polymerization of acrylic acid blended with sodium hydroxide in the presence of an initiator.

Other superabsorbent polymers include polyacrylamide copolymer, ethylene maleic anhydride copolymer, cross-linked carboxymethylcellulose, polyvinylalcohol copolymers, cross-linked polyethylene oxide, starch-grafted copolymers of polyacrylonitrile, and others.

Another class of superabsorbent polymer that may be used in the invention is alginate, ie salts of alginic acid. Such material occurs naturally as a viscous gum that is abundant in the cell walls of brown algae, and commercial forms are extracted from seaweed. Alginic acid is a linear copolymer with homopolymeric blocks of (1-4)-linked β-D-mannuronate and its C-5 epimer α-L-guluronate residues, covalently linked together in different sequences or blocks. Alginates that are particularly suitable for use in the present invention are calcium alginate and sodium alginate.

When the device is in use, fluid comprising discrete or particulate material dispersed in a liquid medium passes through a port in the outer bag and enters the cavity between the outer and inner bag. The liquid medium may then pass through the permeable wall of the inner bag and be held there by the absorbent material, preventing it from passing back into the cavity between the outer and inner bags. As a result, particles that are too large to pass through the wall of the permeable inner bag are concentrated in the cavity. The resulting concentrated fluid may then be removed from the device, and the device disposed of.

The liquid medium removed from the fluid during the concentration process is difficult to recover from the absorbent material. This is undesirable where the liquid medium is valuable, such as in the case of blood plasma, which is removed from whole blood during the production of blood cell concentrates.

Therefore, according to a second aspect of this invention, there is provided a fluid concentration device comprising an outer bag formed of an impermeable material and an inner bag formed of a permeable material, wherein the inner bag is adapted for connection to a source of reduced pressure.

The device of this aspect of the invention is advantageous primarily in that it provides a simple and inexpensive means of effectively concentrating fluids comprising discrete or particulate material dispersed in a liquid medium by removal of the liquid medium, which readily allows recovery of the liquid medium that is removed.

The preferred materials and structure of the outer and inner bags of the device of this aspect of the invention are substantially the same as for the device of the first aspect of the invention.

The inner bag preferably presents the largest possible effective surface area on the interior of the device. The inner bag is therefore preferably suspended within and fastened to the outer bag to prevent the inner bag from slumping or collapsing.

Inner bag is preferably completely sealed, other than the means by which it is connected to the source of reduced pressure, so the liquid medium is only able to enter the inner bag by passing through its porous walls.

The means by which the inner bag is coupled to the source of reduced pressure is preferably a drainage conduit by which liquid medium drawn from the fluid in the outer bag can be drained from the device. The drainage conduit may be formed of any suitable material, but is preferably formed of a flexible plastics material. In one particularly preferred embodiment, the drainage conduit enters the device through a port in the outer bag and connects directly to the inner bag via a connector. The connector preferably forms a secure fastening between the drainage conduit and the inner bag to prevent leakage from the connection. This may be achieved by the connector having a flange portion, which provides a larger surface area for fastening to the inner bag.

The drainage conduit preferably extends from the device and has a free end that can be attached to a vacuum pump or the like. A collection vessel may be interposed between the drainage conduit and the vacuum pump, to enable the collection of fluid drawn from the device.

The inner bag preferably contains a wadding material to prevent it collapsing upon the application of a reduced pressure and ensure an even distribution of pressure throughout the inner bag. The wadding material is preferably a foam or non-woven fabric material, but may be any material that is sufficiently porous to allow fluid to pass through freely without clogging, and is sufficiently resilient to prevent the inner bag collapsing.

In use, fluid is introduced into the device through a port in the outer bag and enters the cavity between the outer and inner bags. Reduced pressure applied to the inner bag draws fluid through the permeable wall of the inner bag from the cavity, and carries it away from the device, resulting in the concentration of particles that are too large to pass through the porous wall of the inner bag in the cavity. The resulting concentrated fluid may be removed from the device through a port in the outer bag and the device disposed of or re-used.

The device according to this aspect of the invention is of particular utility in the field of medicine to produce blood cell concentrates from whole blood by the removal of a proportion of the plasma component, as it allows the blood plasma to be recovered easily.

Therefore, according to a third aspect of this invention, there is provided a method of processing blood, which method comprises contacting blood with the first side of a porous screen having a first side and a second side, and applying a pressure differential across the porous screen such that the blood plasma is drawn through the porous screen.

The pressure differential applied across the porous screen draws at least blood plasma through the porous screen, while at least the blood cells remain on the first side of the porous screen.

The method of this invention is advantageous primarily in that it provides a simple and inexpensive means of efficiently processing blood to produce blood cell concentrates and it allows the blood plasma removed from the blood to be recovered easily from the second side of the porous screen.

The pressure differential across the porous screen may be generated by any suitable means, although it is preferably generated by applying a reduced pressure to the second side of the screen with the use of a pressure reducing means. The means employed to generate the reduced pressure preferably takes the form of a vacuum pump or the like.

The pressure differential across the porous screen must be of sufficient magnitude to draw at least blood plasma through the porous screen, but is preferably not so great as to damage the blood cells or porous screen.

The pressure differential is preferably applied continuously and may be applied in conjunction with agitation to facilitate the transmission of at least the plasma component of blood through the porous screen.

In general, the properties of the porous screen determine what components of the blood are removed by the method of the present invention.

The method of this invention may employ a porous screen which only allows the transmission of the blood plasma, such that all particulate matter remains on the first side of the porous screen, in which case the pores of the porous screen may be up to 1 µm in diameter. Alternatively, the method of this invention may employ a porous screen that allows small particulate matter, such as thrombocytes (platelets), to pass through, such that only larger particulate matter, such as erythrocytes (red blood cells), remain on the first side of the porous screen. The pores of the porous screen may therefore be up to 3 µm in diameter, or up to 5 µm in diameter.

The method of this invention may further comprise a step of processing the blood cell concentrate to remove a particular category of blood cells. For example, leukocytes (white blood cells) may be removed from the blood cell concentrate to leave a blood cell concentrate substantially consisting of erythrocytes (red blood cells). This may be carried out by passing the blood cell concentrate through a leukocyte reduction filter, which are well-known in the field.

The method of this invention may also comprise a further step of collecting the plasma, and whatever other components of the blood that are drawn through the porous screen. This may be carried out by placing a receptacle between the second side of the porous screen and the pressure reducing means, such that whatever components of the blood are drawn through the porous screen are collected in the receptacle.

Blood cell concentrates produced by the method of this invention are preferably suitable for administration to a patient and are therefore kept free from contamination with microorganisms. Accordingly, the method of this invention may additionally comprise an initial step of introducing the blood into a sterile device that houses the porous screen, the method of the invention thereby being carried out within that device to prevent contamination with microorganisms. The interior of any such device is preferably partitioned by the porous screen into a first chamber on the first side of the porous screen and a second chamber on the second side of the porous screen.

The method of this invention is preferably carried out using the device of the second aspect of this invention.

Whole blood may be introduced into the device through an inlet, which preferably takes the form of a port that connects the first chamber with the exterior of the device. The blood cell concentrate may be drained from the device via a separate outlet that connects the first chamber with the exterior of the device. Where a separate inlet and outlet are present, blood may be passed through the device continuously such that the method of this invention is carried out as a continuous process. However, the method of this invention is preferably carried out as a batch process, in which the device is charged with blood via the inlet, with the outlet sealed, and the concentrated blood subsequently drained from the device by opening of the outlet. In the case of a batch process, fluid may be introduced into and drained from the device through the same port, so a separate inlet and outlet are not necessarily.

The proportion of plasma that is removed from an amount of blood by the method of this invention is dependent on the magnitude of the pressure differential across the porous screen, and the length of time that pressure differential is applied. Where the method of this invention is carried out as a continuous process, the proportion of plasma that is removed from an amount of blood is also dependent of the flow rate of the blood. In general, it is possible to produce more highly concentrated blood cell concentrates when the method of this invention is carried out as a batch process.

BRIEF DESCRIPTION OF THE DRAWINGS

Currently preferred embodiments of the invention will now be described, by way of illustration only, with reference to the accompanying drawings, in which.

Figure 1:
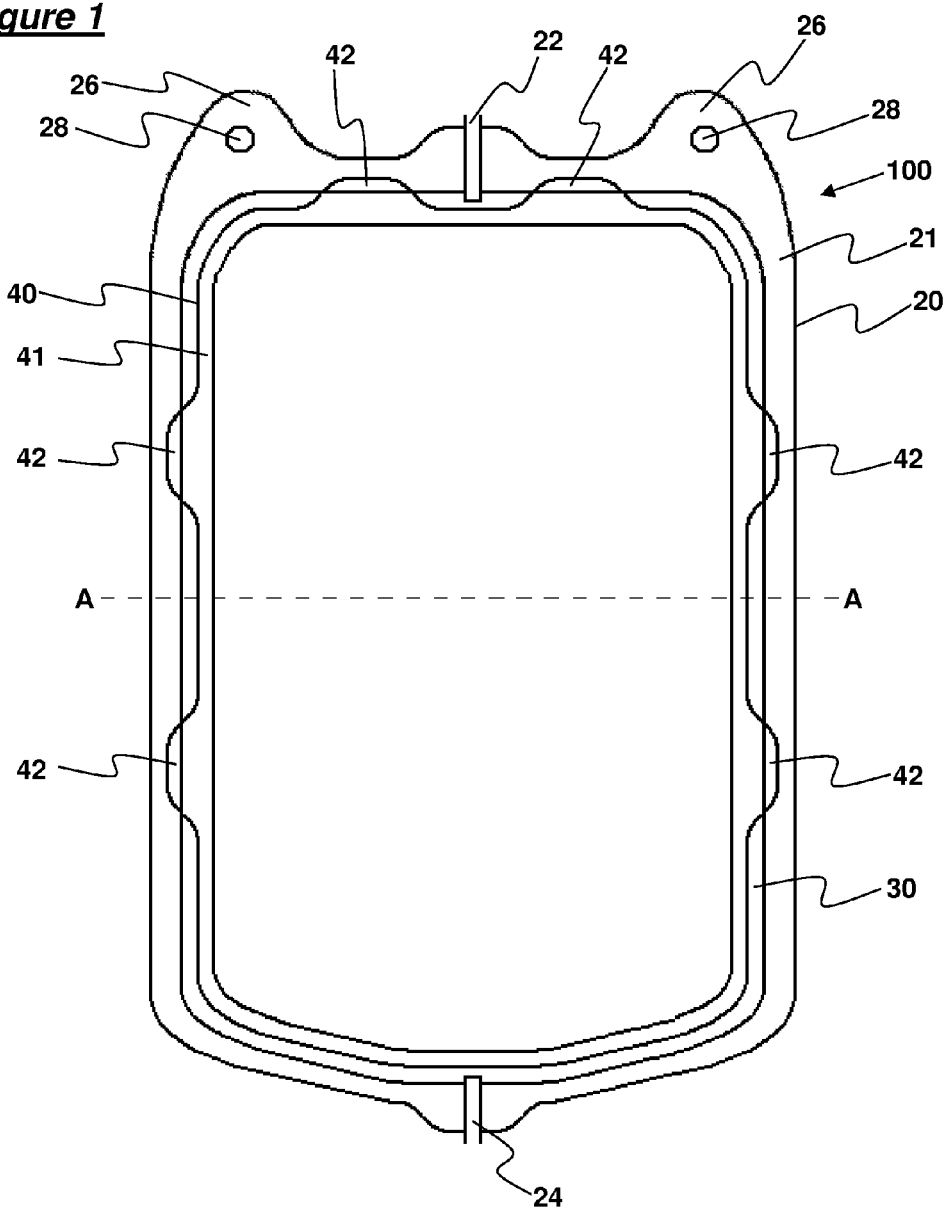
FIG. 1 is a side elevation of an embodiment of a fluid concentration device according to the first aspect of the invention.
Figure 2:
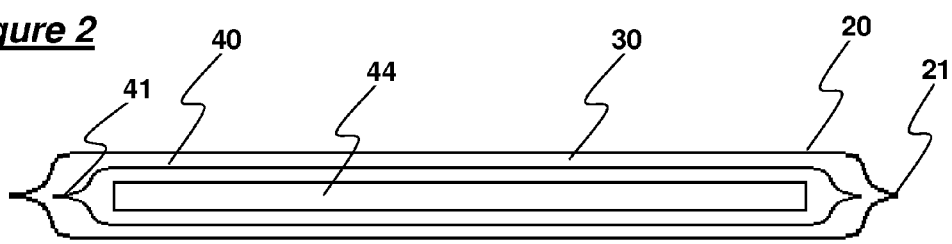
FIG. 2 is a cross sectional view of the fluid concentration device of FIG. 1, taken along axis A-A.

Referring first to FIGS. 1 and 2, an embodiment of a fluid concentration device according to the first aspect of the invention is generally designated 100. The device 100 is for concentrating fluids comprising discrete or particulate material dispersed in a liquid medium by removal of a proportion of the liquid medium. The device 100 comprises an outer bag 20 formed of a tough impermeable material, an inner bag 40 formed of a porous material and contained within the outer bag 20, and an absorbent material 44 encapsulated within the inner bag 40. The outer bag has an inlet port 22, through which fluid may pass into the device 100 and enter cavity 30 formed between the outer bag 20 and the inner bag 40, and an outlet port 24, though which fluid may exit the device 100.

The presence of both an inlet port 22 and an outlet port 24 in the outer bag 20 enables fluid to flow though the device 100 continuously, allowing fluid concentration to be carried out as a continuous process. Fluid concentration may also be carried out in a batch process, in which the device 100 is charged with fluid via the inlet port 22, with the outlet port 24 sealed. The fluid held in the device 100 may then be concentrated and subsequently drained from the device 100 by opening the outlet port 24. However, it should be appreciated that other embodiments of the device 100 for concentrating fluid in a batch process may have only a single port through which fluid is both introduced into and drained from the device 100.

The outer bag 20 is formed of polyvinylchloride (PVC) sheets and the inner bag 40 is formed of porous polycarbonate membrane. Both the outer bag 20 and inner bag 40 are formed by fastening two sheets of material together around their edges by heat welding. The material of the outer bag 20 is impermeable to the liquid medium of the fluid introduced into the device 100. The material of the inner bag 40 permits liquid medium, but not the discrete or particulate material, to pass through it and into the interior of the inner bag 40. For instance, where the device 100 is for producing blood cell concentrates from whole blood, the inner bag 40 is formed of material having pores with a maximum size of no greater than 5 μm to permit blood plasma, but not red blood cells, to pass through.

The area around the edge of the outer bag 20 where the two polyvinylchloride (PVC) sheets are welded together defines a welded portion 21. This welded portion 21 projects from each upper corner of the outer bag 20 to form extensions 26. Each extension 26 has an aperture 28 to allow the device 100 to be hung from a suitable support.

The area around the edge of the inner bag 40 where the two porous polycarbonate membranes are welded together also defines a welded portion 41. The absorbent material 44 is entirely encapsulated by the inner bag 40. The welded portion 41 around the edge of the inner bag 40 extends outwardly to form a number of tabs 42, which are fastened to the interior of the outer bag 20 at a number of points to suspend the inner bag 40 within the outer bag 20 (described in more detail below with reference to FIG. 5).

In use, a fluid comprising discrete or particulate material dispersed in a liquid medium is introduced into the device 100 through the inlet port 22 in the outer bag 20 and enters the cavity 30 between the outer 20 and inner bag 40. The inlet 22 and outlet 24 ports are then sealed to prevent the fluid escaping the device during the concentration process. Fluid contained in cavity 30, passes through the porous walls of the inner bag 40 and is held there by the absorbent material 44, thereby increasing the concentration of the discrete or particulate material in the cavity 30. The device 100 may be gently agitated during the concentration process to facilitate passage of the liquid medium through the porous walls of the inner bag 40. Following concentration, the concentrated fluid contained in cavity 30 may be drained from the device via the outlet port 24, and the device disposed of.

Figure 3:
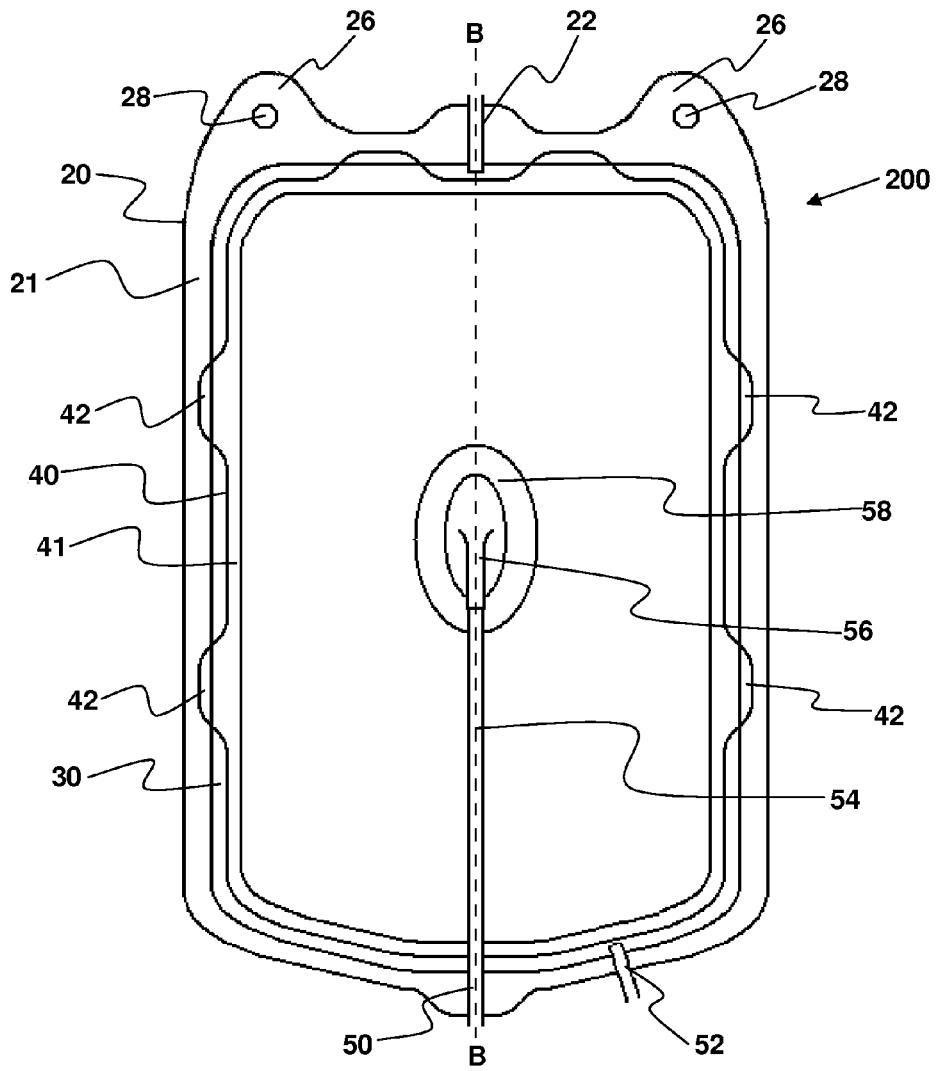
FIG. 3 is a side elevation of an embodiment of a fluid concentration device according to the second aspect of the invention.
Figure 4:
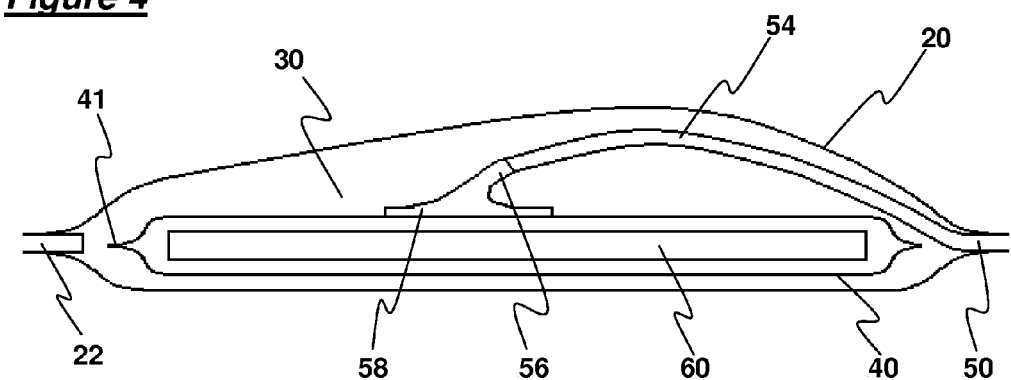
FIG. 4 is a cross sectional view of the fluid concentration device of FIG. 2, taken along axis B-B.

Referring now to the FIGS. 3 and 4, an embodiment of a fluid concentration device according to the second aspect of the invention is generally designated 200. The device 200 comprises an outer bag 20 formed of a tough impermeable material, an inner bag 40 formed of a porous material and contained within the outer bag 20, and a wadding material 60 contained within the inner bag 40.

Both the outer bag 20 and the inner bag 40 are formed by heat welding two sheets of material together in the welded portions 21, 41 around their edges. The welded portion 21 at each upper corner of the outer bag 20 form extensions 26, each having an aperture 28 to allow the device 200 to be hung from a suitable support. The welded portion 41 of the inner bag 40 forms a number of tabs 42, which are fastened to the interior of the outer bag 20 at a number of points to suspend the inner bag 40 within the outer bag 20 (described in more detail below with reference to FIG. 5).

The device 200 has an inlet port 22, through which fluid may enter the device 200, and a drainage port 52, through which concentrated fluid may be drained from the device 200. The presence of both an inlet port 22 and a drainage port 52 in the outer bag 20 enables fluid to flow though the device 100 continuously, allowing fluid concentration to be carried out as a continuous process. Fluid concentration may also be carried out in a batch process, in which the device 100 is charged with fluid via the inlet port 22, with the outlet port 24 sealed. The fluid held in the device 100 may then be concentrated and subsequently drained from the device 100 by opening the outlet port 24. However, it should be appreciated that other embodiments of the device 100 for concentrating fluid in a batch process may have only a single port through which fluid is both introduced into and drained from the device 100.

The device 200 also has a vacuum port 50, through which one end of a vacuum conduit 54 enters the device 200 and connects directly with the interior of the inner bag 40. The other end of the vacuum conduit 54 is free to be connected to a source of reduced pressure such as a vacuum pump (not shown). The vacuum conduit 54 is formed of a flexible plastics material and connects to the inner bag 40 via a coupling that is formed of a tough plastics material and comprises a channel portion 56, through with the drainage conduit communicates with the interior of the inner bag 40, and a flange portion 58, which contacts the surface of the inner bag 40 and provides an increased surface area to improve fastening with the inner bag 40. The inner bag 40 is entirely sealed other than its connection with the drainage conduit 54.

In use, a fluid comprising discrete or particulate material dispersed in a liquid medium is introduced into the device 200 through the inlet port 22 and enters the cavity 30 formed between the outer 20 and inner bags 40. The inlet port 22 and drainage port 52 are then sealed to prevent the fluid escaping the device 200 during the concentration process.

The free end of the vacuum conduit 54 is connected to a source of reduced pressure, which applies a reduced pressure to the inner bag 40. The wadding material 60 prevents the inner bag 40 collapsing when the reduced pressure is applied, ensuring an even distribution of pressure throughout the inner bag 40. The reduced pressure draws liquid medium and any discrete or particulate material of a small enough diameter from the cavity 30, through the porous walls of the inner bag 40 into the interior of the inner bag 40. Liquid that enters the inner bag 40 is then drawn along the vacuum conduit 54 and into a receptacle (not shown) from which it can be collected. Particles that are too large to pass through the porous walls of the inner bag 40 remain in the cavity 30, resulting in those particles being concentrated in that portion of the device 200. The device 200 may also be gently agitated during the concentration process to facilitate passage of the liquid medium through the porous walls of the inner bag 40. Following concentration, the concentrated fluid contained in the cavity 30 may be drained from the device 200 via the drainage port 52, and the device 200 disposed of or re-used.

Figure 5:
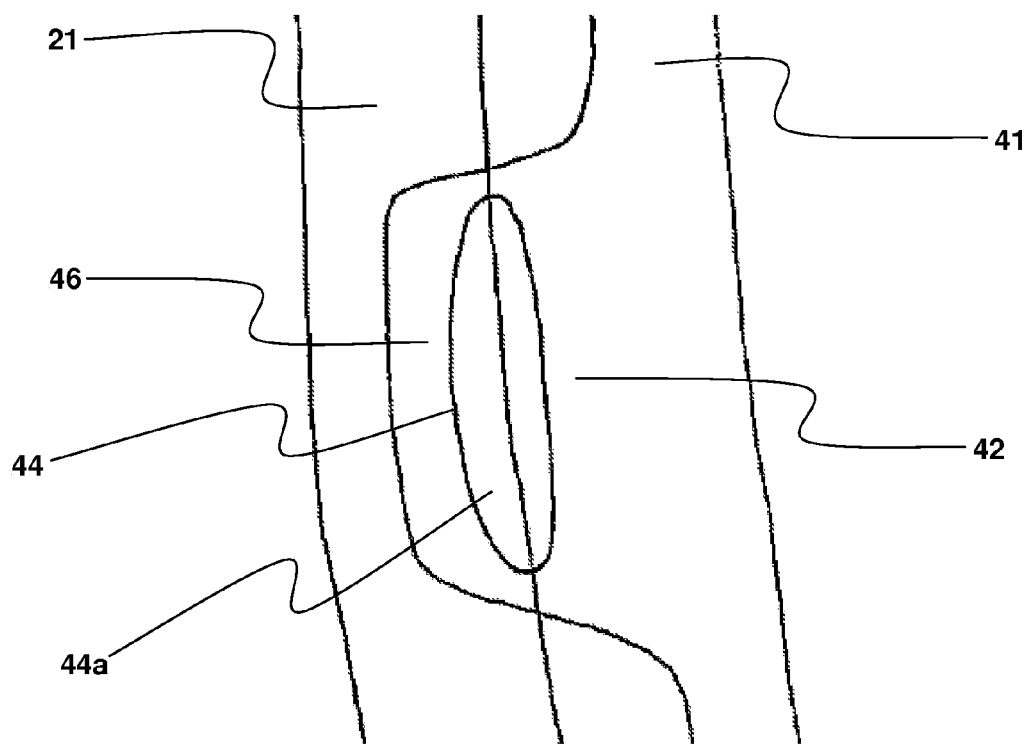
FIG. 5 is a view on an enlarged scale of a fastening point where inner and outer bags of a fluid concentration device are fastened together.

Referring now to FIG. 5, a view on an enlarged scale of a fastening point between an inner bag 40 and an outer bag 20 is depicted. The fastening point comprises a tab 42 having an opening 44 and a loop section 46. During manufacture of a device 100, 200 according to this invention, the pre-formed inner bag is positioned between the two layers of material that form the outer bag 20. The tabs 42 are located such that the loop section 46 and the outer region 44a of the aperture 44 are within the region that will become the welded portion 21 of the outer bag 20. The two layers of the outer bag 20 weld together through the outer region 44a of the aperture 44, thereby encapsulating the loop section 46 within the welded portion 21. The inner bag 40 is therefore securely fastened to the outer bag 20 even where the material of the inner bag 40 and the outer bag 20 do not weld strongly to one another.

The invention claimed is:

1. A fluid concentration device for concentrating fluids comprising particulate material dispersed in a liquid medium by removal of a proportion of the liquid medium, the device comprising:
   an outer bag formed of two layers of an impermeable material fastened together around their edges;
   an inner bag fastened to an inner wall of the outer bag at one or more fastening points, wherein the one or more fastening points consist of a tab projecting from an edge of the inner bag and sandwiched between the two layers of the outer bag where they are welded together, wherein each tab has one or more apertures, the inner bag being suspended within the outer bag and formed of a permeable material; and a port in the outer bag for introducing fluid into the cavity between the outer and inner bags, wherein the permeable material allows the liquid medium, but not the particulate material, to pass into the inner bag, and the inner bag contains an absorbent material for holding the liquid medium in the inner bag.

2. The fluid concentration device of claim 1, wherein the absorbent material is a superabsorbent material.

3. The fluid concentration device of claim 2, wherein the superabsorbent material is a polyacrylate.

4. The fluid concentration device of claim 1, wherein the materials of the inner and outer bags are flexible.

5. The fluid concentration device of claim 1, wherein the materials of the inner and outer bags are heat weldable.

6. The fluid concentration device of claim 5, wherein the inner bag and the outer bag are formed of two sheets of material fastened together around their edges by heat welding.

7. The fluid concentration device of claim 1, wherein the material of the outer bag is polyvinylchloride.

8. The fluid concentration device of claim 1, wherein the material of the inner bag is porous polycarbonate membrane.

9. The fluid concentration device of claim 1, wherein the inner bag is formed of a permeable material with pores that have a diameter of between 0.01 μm and 1 mm.

* * * * *